United States Patent
Akiba et al.

(10) Patent No.: US 10,506,916 B2
(45) Date of Patent: Dec. 17, 2019

(54) ENDOSCOPIC SYSTEM AND IMAGE PROCESSING DEVICE

(71) Applicant: OLYMPUS CORPORATION, Hachioji-shi, Tokyo (JP)

(72) Inventors: Hirotaka Akiba, Tokyo (JP); Daisuke Sano, Yokohama (JP); Hiroyuki Ushifusa, Tokyo (JP); Hiroshi Tamai, Tokyo (JP); Noriyuki Takeishi, Tokyo (JP); Hisashi Yoda, Tokyo (JP); Tadao Eto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 174 days.

(21) Appl. No.: 15/414,042

(22) Filed: Jan. 24, 2017

(65) Prior Publication Data

US 2017/0127908 A1    May 11, 2017

Related U.S. Application Data

(63) Continuation of application No. PCT/JP2015/070791, filed on Jul. 22, 2015.

(30) Foreign Application Priority Data

Jul. 28, 2014 (JP) .................................. 2014-152848

(51) Int. Cl.
*A61B 1/00* (2006.01)
*A61B 1/045* (2006.01)

(52) U.S. Cl.
CPC ........ *A61B 1/00022* (2013.01); *A61B 1/0002* (2013.01); *A61B 1/00009* (2013.01);
(Continued)

(58) Field of Classification Search
CPC ............ A61B 1/00022; A61B 1/00009; A61B 1/00057; A61B 1/00059; A61B 1/045;
(Continued)

(56) References Cited

U.S. PATENT DOCUMENTS

| 4,996,975 A | 3/1991 | Nakamura |
| 6,538,687 B1 | 3/2003 | Saito et al. |
(Continued)

FOREIGN PATENT DOCUMENTS

| JP | H03-4831 A | 1/1991 |
| JP | H11-42211 A | 2/1999 |
(Continued)

OTHER PUBLICATIONS

Oct. 27, 2015 International Search Report issued in International Patent Application No. PCT/JP2015/070791.
(Continued)

*Primary Examiner* — Timothy J Neal
*Assistant Examiner* — William B Chou
(74) *Attorney, Agent, or Firm* — Oliff PLC

(57) ABSTRACT

An endoscopic system includes an endoscope that obtains image information inside a subject; a first recording medium into which the image information obtained from the endoscope is written; a second recording medium that has a table in which a recording condition for writing the image information obtained from the endoscope into the first recording medium has been recorded; and a controller that obtains, on the basis of an operation time period obtained from the endoscope, a recording condition associated with the obtained operation time period from among the plurality of recording conditions recorded in the table that the second recording medium has, and records the image information in the first recording medium under the recording condition.

9 Claims, 6 Drawing Sheets

(52) U.S. Cl.
CPC .......... *A61B 1/045* (2013.01); *A61B 1/00006* (2013.01); *A61B 1/00011* (2013.01); *A61B 1/00025* (2013.01); *A61B 1/00036* (2013.01)

(58) Field of Classification Search
CPC ... A61B 1/0002; A61B 1/00036; A61B 1/128; A61B 1/04; A61B 1/00011; A61B 5/7232
USPC ........................................................ 600/118
See application file for complete search history.

(56) References Cited

U.S. PATENT DOCUMENTS

| | | | |
|---|---|---|---|
| 2002/0101507 A1 | 8/2002 | Saito et al. | |
| 2002/0196334 A1 | 12/2002 | Saito et al. | |
| 2003/0122927 A1 | 7/2003 | Saito et al. | |
| 2004/0107113 A1 | 6/2004 | Araki | |
| 2007/0255155 A1* | 11/2007 | Drew | A61B 5/0028 600/523 |
| 2008/0309481 A1* | 12/2008 | Tanaka | A61B 5/0002 340/539.12 |
| 2010/0094312 A1* | 4/2010 | Ruiz Morales | B25J 13/085 606/130 |
| 2011/0082377 A1* | 4/2011 | Mahajan | A61B 5/0002 600/508 |
| 2012/0242812 A1* | 9/2012 | Koizumi | A61B 1/00009 348/65 |
| 2013/0083179 A1* | 4/2013 | Kotani | H04N 5/217 348/65 |
| 2014/0063215 A1* | 3/2014 | Miura | A61B 1/0002 348/65 |
| 2015/0141758 A1* | 5/2015 | Kagawa | A61B 1/0684 600/178 |
| 2017/0095667 A1* | 4/2017 | Yakovlev | A61N 1/36125 |

FOREIGN PATENT DOCUMENTS

| | | |
|---|---|---|
| JP | 2002-177212 A | 6/2002 |
| JP | 2004-129727 A | 4/2004 |
| JP | 2004-174008 A | 6/2004 |
| JP | 2004-337404 A | 12/2004 |
| JP | 2005-160724 A | 6/2005 |
| JP | 2007-151789 A | 6/2007 |
| JP | 2010-051399 A | 3/2010 |

OTHER PUBLICATIONS

Sep. 6, 2016 Office Action issued in Japanese Patent Application No. 2016-525625.
Oct. 27, 2015 Written Opinion issued in International Patent Application No. PCT/JP2015/070791.

* cited by examiner

| RECORDING ITEM | TOTAL ENERGIZING TIME PERIOD OF ENDOSCOPE | | |
|---|---|---|---|
| | ~100 HOURS | 100~5000 HOURS | 5000 HOURS~ |
| MOVING IMAGE DENSITY | 5Mbps | NOT RECORDED | 10Mbps |
| LOG A FREQUENCY | 300sec | NOT RECORDED | 300sec |
| LOG B FREQUENCY | 30sec | 60sec | 30sec |

FIG 2

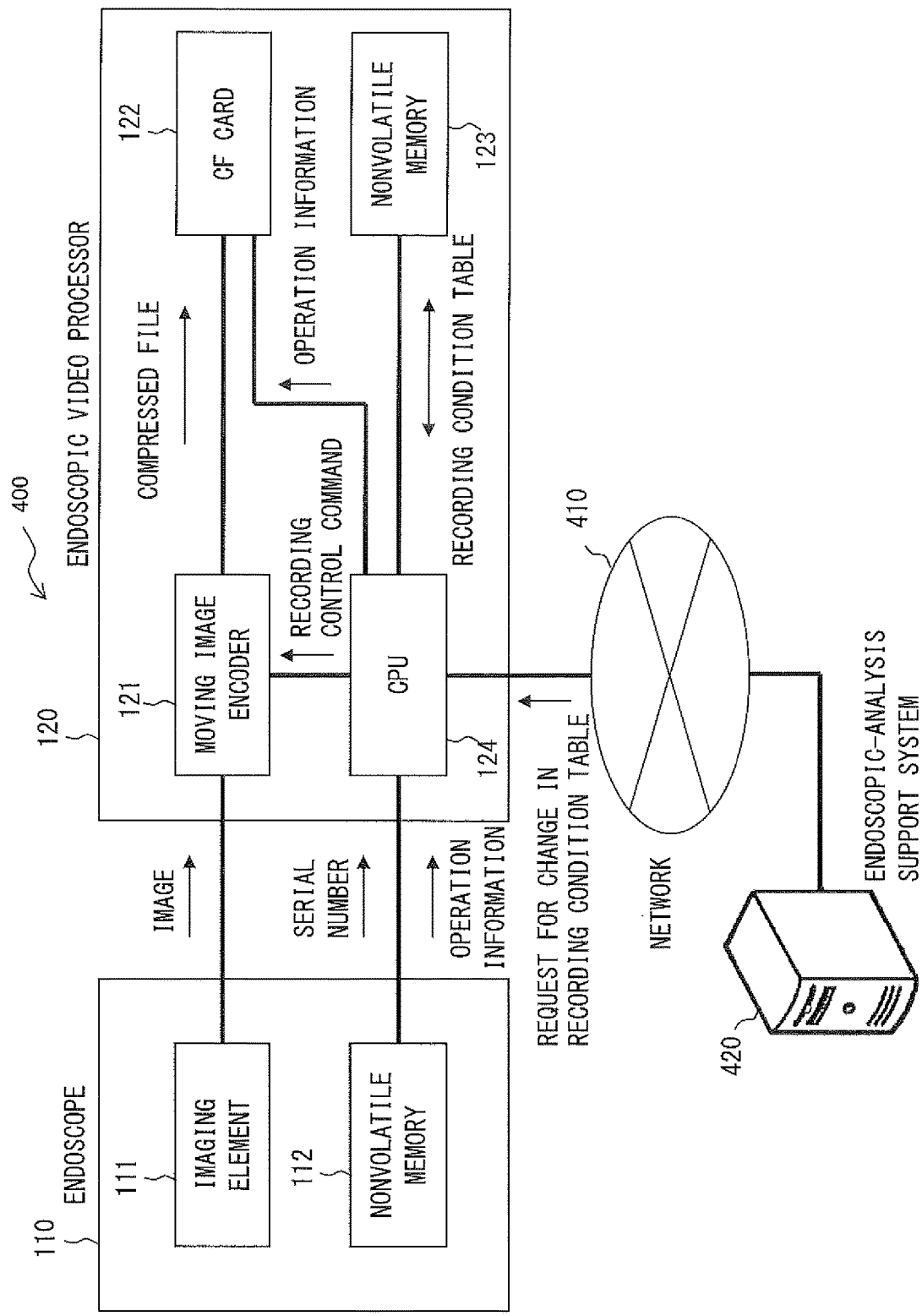
F I G. 5

| SERIAL NUMBER OF ENDOSCOPE | RECORDING ITEM | TOTAL ENERGIZING TIME PERIOD OF ENDOSCOPE | | |
|---|---|---|---|---|
| | | ~100 HOURS | 100~5000 HOURS | 5000 HOURS~ |
| ○○○○○ | MOVING IMAGE DENSITY | 5Mbps | NOT RECORDED | 10Mbps |
| △△△△△ | MOVING IMAGE DENSITY | 5Mbps | NOT RECORDED | 5Mbps |
| ××××× | MOVING IMAGE DENSITY | 10Mbps | NOT RECORDED | 10Mbps |
| ⋮ | ⋮ | ⋮ | ⋮ | ⋮ |

F I G. 6

ENDOSCOPIC SYSTEM AND IMAGE PROCESSING DEVICE

CROSS-REFERENCE TO RELATED APPLICATIONS

This application is based upon and claims the benefit of priority of the prior Japanese Patent Application No. 2014-152848, filed Jul. 28, 2014, the entire contents of which are incorporated herein by reference.

This is a Continuation application of PCT Application No. PCT/JP2015/070791, filed Jul. 22, 2015, which was not published under PCT Article 21(2) in English.

FIELD

The present invention relates to an endoscopic system including an endoscope and an image processing device.

BACKGROUND

Conventionally, there is an endoscopic system that includes an endoscope (a scope) that captures an image of a subject and an image processing device that processes an image obtained by the endoscope and performs, for example, a recording of the processed image.

For example, there is an image recording device that is connected to an endoscope and performs an operation such as automatically starting or terminating a recording of an endoscopic image on the basis of a result of a detection performed by a red-color detector included in the image recording device (see Japanese Laid-open Patent Publication No. 2010-51399). For example, there is also an electronic endoscopic system that includes a scope and an image signal processing unit and performs an operation such as stopping a recording if a connection between the scope and the image signal processing unit has been released for more than a predetermined time period since the recording was started (see Japanese Laid-open Patent Publication No. 2002-177212).

In the operation of an endoscopic system, a determination of the occurrence of a failure in an endoscope is performed when the occurrence of the failure is suspected. The determination of the occurrence of a failure in an endoscope is often performed on the basis of a video obtained by an endoscope in which the occurrence of the failure is suspected and by an image processing device that was used along with the endoscope.

SUMMARY

An aspect of the present invention provides an endoscopic system including: an endoscope that obtains image information inside a subject; a first recording medium into which the image information obtained from the endoscope; a second recording medium that has a table in which a recording condition for writing the image information obtained from the endoscope into the first recording medium has been recorded, wherein a plurality of different recording conditions that are each associated with an operation time period of the endoscope are recorded in the table; and a controller that obtains, on the basis of an operation time period obtained from the endoscope, a recording condition associated with the obtained operation time period from among the plurality of recording conditions recorded in the table that the second recording medium has, and records the image information in the first recording medium under the recording condition.

Another aspect of the present invention provides an image processing device that is configured to be connected to an endoscope and obtains image information inside a subject from the endoscope, the image processing device including: a first recording medium into which the image information obtained from the endoscope is written; a second recording medium that has a table in which a recording condition for writing the image information obtained from the endoscope into the first recording medium has been recorded, wherein a plurality of different recording conditions that are each associated with an operation time period of the endoscope are recorded in the table; and a controller that obtains, on the basis of an operation time period obtained from the endoscope, a recording condition associated with the obtained operation time period from among the plurality of recording conditions recorded in the table that the second recording medium has, and records the image information in the first recording medium under the recording condition.

BRIEF DESCRIPTION OF DRAWINGS

FIG. 2 illustrates an example of a recording condition table according to the first embodiment;

FIG. 5 illustrates an example of a configuration of the endoscopic system according to a fourth embodiment; and FIG. 6 illustrates an example of a recording condition table according to the fourth embodiment.

DESCRIPTION OF EMBODIMENTS

Embodiments will now be described with reference to the drawings.

First Embodiment

Figure 1:
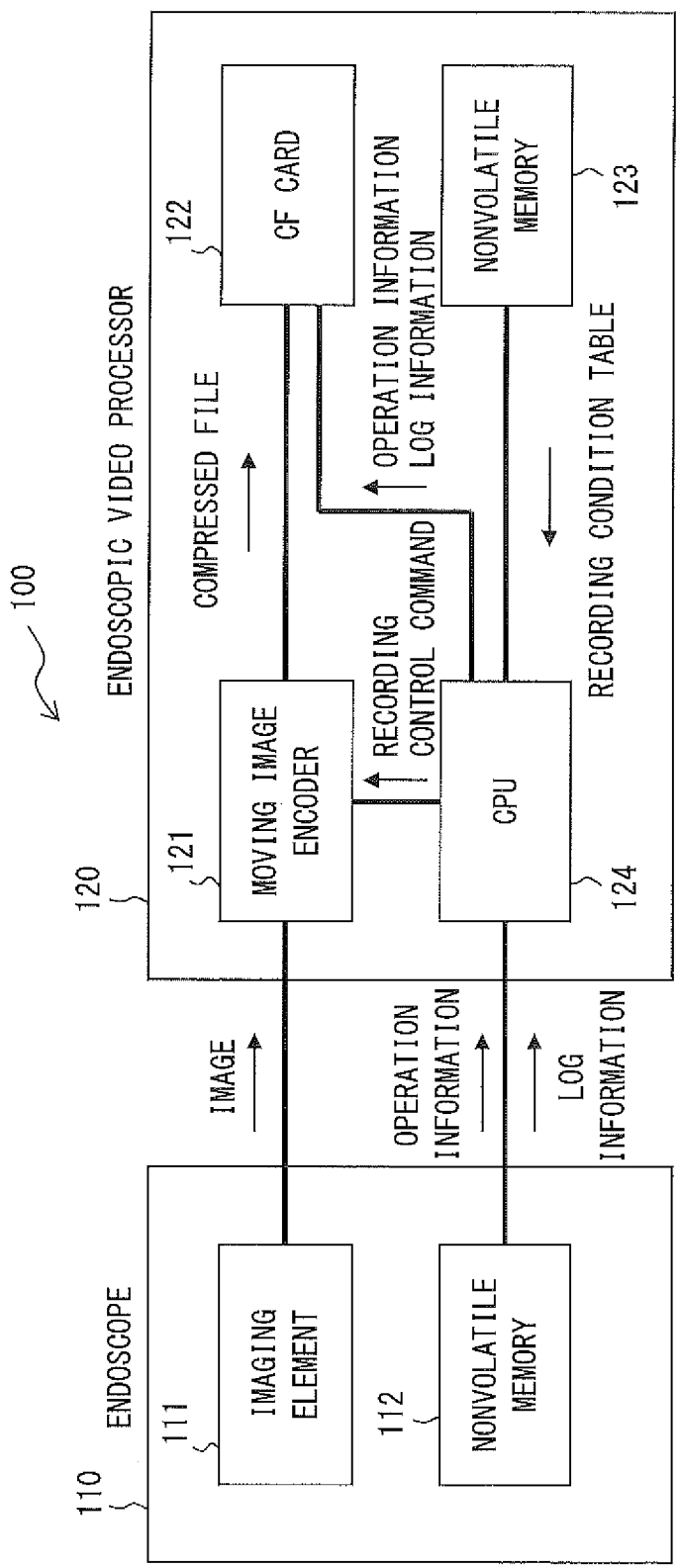
FIG. 1 illustrates an example of a configuration of an endoscopic system according to a first embodiment.

FIG. 1 illustrates an example of a configuration of an endoscopic system according to a first embodiment of the present invention.

As illustrated in FIG. 1, an endoscopic system 100 according to the present embodiment includes an endoscope 110 and an endoscopic video processor 120.

The endoscope 110 includes an imaging element 111 and a nonvolatile memory 112.

The imaging element 111 is a solid state imaging element such as a CCD (charge coupled device) image sensor or a CMOS (complementary metal oxide semiconductor) image sensor, and captures an image of a subject and outputs an imaging signal. The imaging signal is also image information obtained by the endoscope 110.

Information such as operation information and log information is recorded in the nonvolatile memory 112.

The operation information recorded in the nonvolatile memory 112 is information on a total energizing time period of the endoscope 110, is obtained by an energizing-time-period accumulator (not illustrated) that is included in the endoscope 110 and includes, for example, a timer, and is constantly updated to newest information. The total energizing time period of the endoscope 110 is a total time period during which the endoscope 110 is energized from the endoscope 110 having been used for the first time until now, and is also a total operation time period of the endoscope 110.

The log information recorded in the nonvolatile memory 112 includes information on a current value and a temperature inside an endoscope. The information on a current value inside an endoscope that is recorded in the nonvolatile memory 112 (hereinafter also referred to as "log A information") is obtained by an overcurrent detector (not illustrated) that is included in the endoscope 110, and is constantly updated to newest information. The overcurrent detector detects overcurrent inside an endoscope (such as the imaging element 111). Further, the information on a temperature inside an endoscope that is recorded in the nonvolatile memory 112 (hereinafter also referred to as "log B information") is obtained by a thermistor anomaly detector (not illustrated) that is included in the endoscope 110, and is constantly updated to newest information. The thermistor anomaly detector detects an anomaly in a temperature inside an endoscope (such as the imaging element 111).

The endoscopic video processor 120 includes a moving image encoder 121, a CF (CompactFlash) card 122, a nonvolatile memory 123, and a CPU (central processing unit) 124.

Under the control of the CPU 124 (according to a recording control command from the CPU 124), the moving image encoder 121 generates a compressed file of a moving image from an imaging signal output from the imaging element 111 of the endoscope 110 and records the compressed file in the CF card 122.

A compressed file of a moving image that is generated by the moving image encoder 121 and information on the endoscope 110, such as operation information and log information, that is output by the CPU 124 are recorded in the CF card 122. The CF card 122 is attachable to and removable from the endoscopic video processor 120.

A recording condition table or the like is recorded in the nonvolatile memory 123. The recording condition table is a table that includes a correspondence relationship between operation information on an endoscope and information on recording conditions for image information and log information obtained from the endoscope. The content of the recording condition table can be changed discretionally by a user through an input unit (not illustrated) of the endoscopic video processor 120. This recording condition table will be described later in detail with reference to FIG. 2.

The CPU 124 controls an overall operation of the endoscope 110 and the endoscopic video processor 120. For example, the CPU 124 controls a recording of image information and log information obtained from the endoscope 110 in the CF card 122 according to a recording condition corresponding to operation information obtained from the endoscope 110, on the basis of the obtained operation information and the recording condition table recorded in the nonvolatile memory 123.

FIG. 2 illustrates an example of the recording condition table.

As illustrated in FIG. 2, the recording condition table is a table that includes a correspondence relationship between operation information on an endoscope (information on a total energizing time period) and information on recording conditions for image information and log information (log A information and log B information) obtained from the endoscope.

In the example of FIG. 2, the total energizing time period of the endoscope is classified into three ranges, less than 100 hours, 100 hours or more to less than 5000 hours, and 5000 hours or more, and the recording conditions for image information, log A information, and log B information obtained from the endoscope are specified corresponding to each of the ranges. For example, the recording condition that corresponds to when the total energizing time period is less than 100 hours is that the image information obtained from the endoscope is recorded as a compressed file of a moving image of 5 Mbps (megabits per second), the log A information obtained from the endoscope is obtained and recorded every 300 sec (seconds), and the log B information obtained from the endoscope is obtained and recorded every 30 sec. The recording condition that corresponds to when the total energizing time period is 100 hours or more to less than 5000 hours is that the log B information obtained from the endoscope is obtained and recorded every 60 sec without the image information and the log A information obtained from the endoscope being obtained or recorded. The recording condition that corresponds to when the total energizing time period is 5000 hours or more is that a moving image obtained from the endoscope is recorded as a compressed file of a moving image of 10 Mbps, the log A information obtained from the endoscope is obtained and recorded every 300 sec, and the log B information obtained from the endoscope is obtained and recorded every 30 sec.

The following operation is performed in the endoscopic system 100 according to the present embodiment that has the configuration described above. For example, image information obtained from the endoscope 110 is processed by the endoscopic video processor 120 so as to record the processed image information in the CF card 122 or display it on a monitor (not illustrated). For example, the following operation is also performed at a predetermined timing (such as when a connection has been established between the endoscope 110 and the endoscopic video processor 120), in order to shorten the time needed for a determination of the occurrence of a failure in the endoscope 110 when the occurrence of the failure is suspected.

First, the CPU 124 of the endoscopic video processor 120 reads operation information from the nonvolatile memory 112 of the endoscope 110 and reads a recording condition table from the nonvolatile memory 123.

Next, the CPU 124 starts a control of a recording of image information and log information obtained from the endoscope 110 according to a recording condition corresponding to the read operation information, on the basis of the read operation information and the read recording condition table. Specifically, the CPU 124 outputs a recording control command to the moving image encoder 121 such that a compressed file of a moving image having a corresponding moving image density (bit rate) is generated from the image information obtained from the endoscope 110 and the compressed file is recorded in the CF card 122. Further, the CPU 124 starts a control to obtain log information from the endoscope and to record the obtained information in the CF card 122 with a corresponding frequency (with a corresponding time period).

For example, when a read total energizing time period (operation information) is 5000 hours or more and the read recording condition table is the recording condition table illustrated in FIG. 2, the CPU 124 outputs a recording control command to the moving image encoder 121 such that a compressed file of a moving image of 10 Mbps is generated and recorded. Further, the CPU 124 starts a control to obtain and record the log A information every 300 sec and to obtain and record the log B information every 30 sec.

The CPU 124 also records, in the CF card 122, the operation information read from the nonvolatile memory 112 of the endoscope 110 at the beginning.

When a predetermined time period has elapsed, the CPU 124 terminates the control described above. Specifically, the CPU 124 outputs a recording control command to the moving image encoder 121 such that the generation and the recording of a compressed file of a moving image are terminated, and terminates the control to obtain and record log information. The predetermined time period can be changed discretionally by the user through the input unit (not illustrated) of the endoscopic video processor 120.

According to the operation described above, operation information on the endoscope 110, a compressed file of a moving image having a moving image density corresponding to the operation information, and log information obtained with a frequency corresponding to the operation information are recorded in the CF card 122.

According to the endoscopic system 100 of the present embodiment, it is possible to perform a determination of the occurrence of a failure in the endoscope 110 when the occurrence of the failure is suspected, by referring to operation information, a compressed file of a moving image, and log information that are recorded in the CF card 122 through the operation described above. Thus, there is no need to collect, as is conventionally done, the endoscope 110 and the endoscopic video processor 120 from a place where the endoscopic system 100 is operated, so it is possible to shorten the time needed for a determination of the occurrence of a failure in the endoscope 110. As a result, it is also possible to shorten the repair lead time for the endoscope 110.

The following is an example of how to perform a determination of the occurrence of a failure in the endoscope 110 on the basis of operation information, a compressed file of a moving image, and log information that are recorded in the CF card 122.

If there is an anomaly in a displayed image when a compressed file of a moving image is played back and if a total energizing time period (operation information) is long, it is possible to determine that a route (such as a transfer route) of the imaging element 111 is a portion in which a failure has occurred. Here, for example, an anomaly in a displayed image is a state in which an image having a large amount of noise is displayed, a state in which an image that has been made monochrome is displayed, or a state in which unintended color bars are displayed. The color bars are a pattern that is displayed, for example, when the endoscope 110 and the endoscopic video processor 120 are not connected.

Further, if there is an anomaly in a displayed image when a compressed file of a moving image is played back and if there is an anomaly in information on a current value (log A information) (if a current value is very high), it is possible to determine that the imaging element 111 is a portion in which a failure has occurred. Here, for example, an anomaly in a displayed image is a state in which an image having a large amount of noise is displayed due to an increase in dark current noise.

Furthermore, if there is an anomaly in a displayed image when a compressed file of a moving image is played back and if there is an anomaly in information on a temperature (log B information) (if a temperature is very high), it is possible to determine that a thermistor or a blurring-prevention device (not illustrated) provided in the endoscope 110 is a portion in which a failure has occurred. Here, for example, an anomaly in a displayed image is a state in which a blurred image is displayed due to a very high temperature.

According to the endoscopic system 100 of the present embodiment, it is also possible to save a recording capacity in the CF card 122 of the endoscopic video processor 120 by including, as information on a recording condition included in a recording condition table, information indicating that a moving image density (bit rate) is to be decreased when image information obtained from the endoscope 110 is recorded, or information indicating that a recording frequency (a time period) of log information obtained from the endoscope 110 is to be shortened, or information indicating that image information and log information are not to be recorded if a total operation time period of the endoscope 110 is within a certain range.

Second Embodiment

Figure 3:
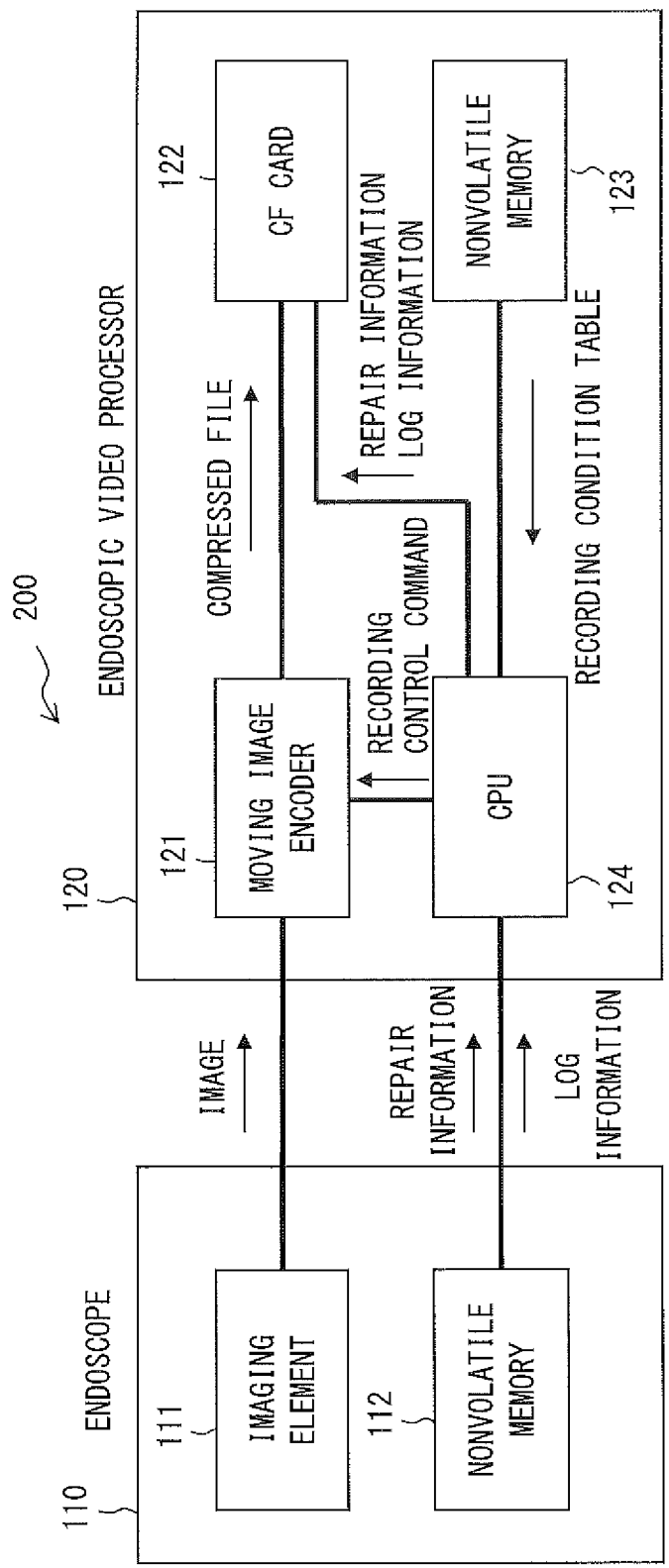
FIG. 3 illustrates an example of a configuration of the endoscopic system according to a second embodiment.

FIG. 3 illustrates an example of a configuration of the endoscopic system according to a second embodiment of the present invention.

For the same components as those in the endoscopic system according to the first embodiment, like reference numbers are used to describe the endoscopic system according to the present embodiment.

As illustrated in FIG. 3, in an endoscopic system 200 according to the present embodiment, repair information on the endoscope 110 is recorded in the nonvolatile memory 112 of the endoscope 110 instead of operation information on the endoscope 110. Alternatively, the repair information on the endoscope 110 may be additionally recorded in the nonvolatile memory 112. The repair information on the endoscope 110 recorded in the nonvolatile memory 112 is information on the number of repairs of the endoscope 110, and is updated every time the endoscope 110 is repaired.

Further, a table that includes a correspondence relationship between repair information on an endoscope and information on recording conditions for image information and log information obtained from the endoscope is recorded in the nonvolatile memory 123 of the endoscopic video processor 120 as a recording condition table. As in the case of the recording condition table of FIG. 2, the recording condition table of this embodiment is configured such that the number of repairs of the endoscope 110 is classified into a plurality of ranges, and the recording conditions for image information, log A information, and log B information obtained from the endoscope are specified corresponding to each of the ranges, although it is not illustrated. The content of the recording condition table can be changed discretionally by a user through the input unit (not illustrated) of the endoscopic video processor 120.

The CPU 124 performs the following control that is a control based on, for example, the recording condition table recorded in the nonvolatile memory 123. The CPU 124 controls a recording of image information and log information obtained from the endoscope 110 in the CF card 122 according to a recording condition corresponding to repair information obtained from the endoscope 110, on the basis of the obtained repair information and the recording condition table recorded in the nonvolatile memory 123.

The other points in the configuration are similar to those in the endoscopic system 100 according to the first embodiment, so their descriptions are omitted.

In the endoscopic system 200 according to the present embodiment, the following operation is performed at a predetermined timing (such as when a connection has been established between the endoscope 110 and the endoscopic video processor 120), in order to shorten the time needed for a determination of the occurrence of a failure in the endoscope 110 when the occurrence of the failure is suspected.

First, the CPU 124 of the endoscopic video processor 120 reads repair information from the nonvolatile memory 112 of the endoscope 110 and reads a recording condition table from the nonvolatile memory 123.

Next, the CPU 124 starts a control of a recording of image information and log information obtained from the endoscope 110 according to a recording condition corresponding to the read repair information, on the basis of the read repair information and the read recording condition table. Specifically, the CPU 124 outputs a recording control command to the moving image encoder 121 such that a compressed file of a moving image having a corresponding moving image density (bit rate) is generated from the image information obtained from the endoscope 110 and the compressed file is recorded in the CF card 122. Further, the CPU 124 starts a control of to obtain log information from the endoscope and to record the obtained information in the CF card 122 with a corresponding frequency (with a corresponding time period).

The CPU 124 also records, in the CF card 122, the repair information read from the nonvolatile memory 112 of the endoscope 110 at the beginning.

When a predetermined time period has elapsed, the CPU 124 terminates the control described above. Specifically, the CPU 124 outputs a recording control command to the moving image encoder 121 such that the generation and the recording of a compressed file of a moving image are terminated, and terminates the control to obtain and record log information. The predetermined time period can be changed discretionally by the user through the input unit (not illustrated) of the endoscopic video processor 120.

According to the operation described above, repair information on the endoscope 110, a compressed file of a moving image having a moving image density corresponding to the repair information, and log information obtained with a frequency corresponding to the repair information are recorded in the CF card 122.

According to the endoscopic system 200 of the present embodiment, it is possible to perform a determination of the occurrence of a failure in the endoscope 110 when the occurrence of the failure is suspected, by referring to repair information, a compressed file of a moving image, and log information that are recorded in the CF card 122 through the operation described above. Thus, as in the case of the endoscopic system 100 according to the first embodiment, it is possible to shorten the time needed for a determination of the occurrence of a failure in the endoscope 110. As a result, it is also possible to shorten the repair lead time for the endoscope 110.

The following is an example of how to perform a determination of the occurrence of a failure in the endoscope 110 on the basis of repair information, a compressed file of a moving image, and log information that are recorded in the CF card 122.

If there is an anomaly in a displayed image when a compressed file of a moving image is played back and if the number of repairs (repair information) is large, it is possible to determine that a failure has occurred again in a portion in which a failure occurred in the past. Here, for example, an anomaly in a displayed image is a state in which an image that has been made monochrome is displayed or a state in which unintended color bars are displayed.

According to the endoscopic system 200 of the present embodiment, it is also possible to save a recording capacity in the CF card 122 of the endoscopic video processor 120 by including, as information on a recording condition included in a recording condition table, information indicating that a moving image density (bit rate) is to be decreased when image information obtained from the endoscope 110 is recorded, or information indicating that a recording frequency (a time period) of log information obtained from the endoscope 110 is to be shortened, or information indicating that image information and log information are not to be recorded if the number of repairs of the endoscope 110 is within a certain range.

Third Embodiment

Figure 4:
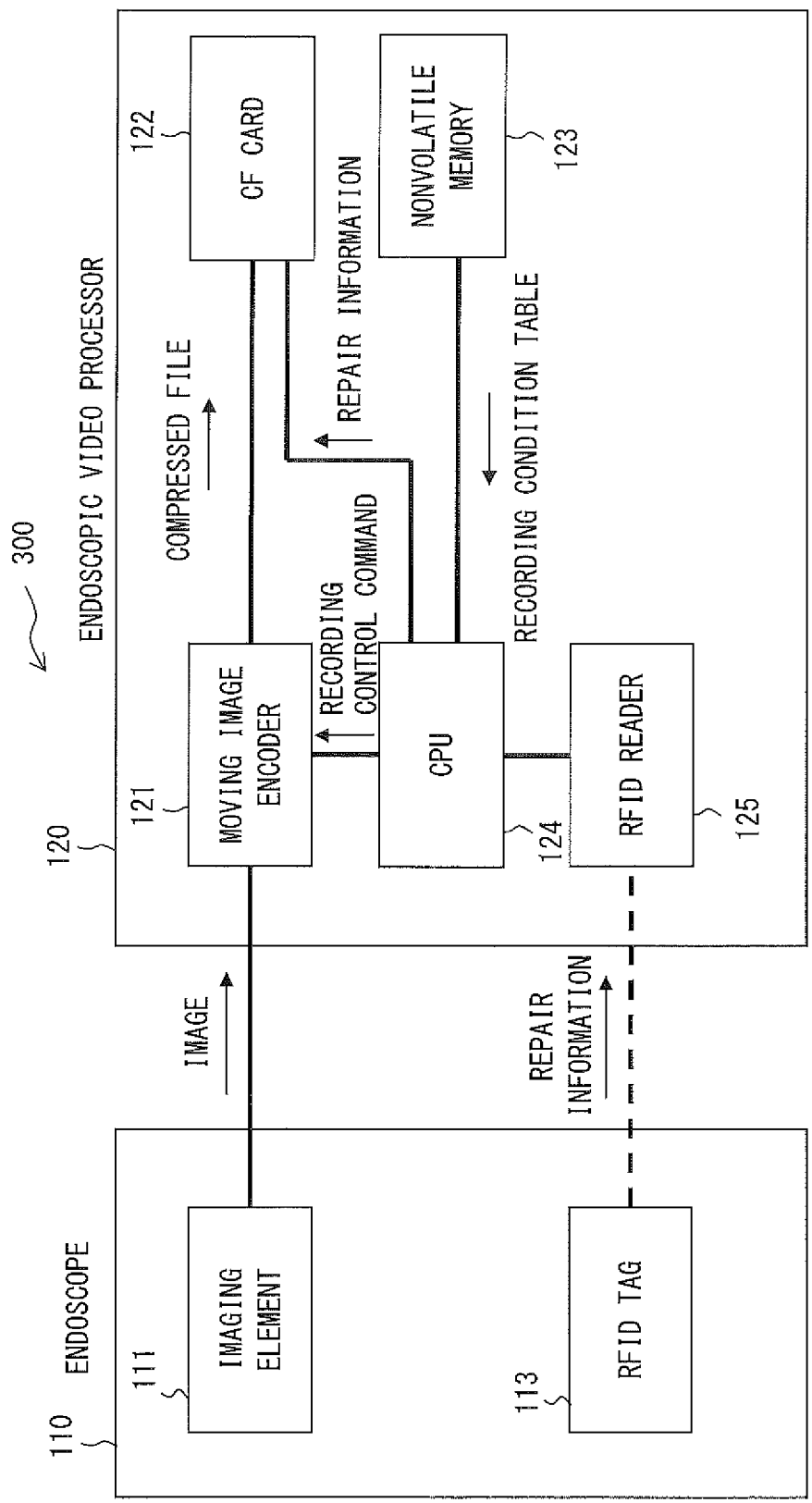
FIG. 4 illustrates an example of a configuration of the endoscopic system according to a third embodiment.

FIG. 4 illustrates an example of a configuration of the endoscopic system according to a third embodiment of the present invention.

For the same components as those in the endoscopic system according to the second embodiment, like reference numbers are used to describe the endoscopic system according to the present embodiment.

As illustrated in FIG. 4, in an endoscopic system 300 according to the present embodiment, the endoscope 110 further includes a RFID (radio frequency identifier) tag 113, and repair information on the endoscope 110 is recorded in the RFID tag 113.

The endoscopic video processor 120 further includes a RFID reader 125, and the RFID reader 125 wirelessly reads the repair information recorded in the RFID tag 113 of the endoscope 110.

Further, a table that includes a correspondence relationship between repair information on an endoscope and information on a recording condition for image information obtained from the endoscope is recorded in the nonvolatile memory 123 of the endoscopic video processor 120 as a recording condition table. As in the case of the recording condition table used in the endoscopic system 200 of the second embodiment, the recording condition table of this embodiment is configured such that the number of repairs of the endoscope 110 is classified into a plurality of ranges, and the recording condition for image information obtained from the endoscope is specified corresponding to each of the ranges, although it is not illustrated. The content of the recording condition table can be changed discretionally by a user through the input unit (not illustrated) of the endoscopic video processor 120.

The CPU 124 performs the following control that is a control based on, for example, the recording condition table recorded in the nonvolatile memory 123. The CPU 124 controls a recording of image information obtained from the endoscope 110 in the CF card 122 according to a recording condition corresponding to repair information read by the RFID reader 125, on the basis of the read repair information and the recording condition table recorded in the nonvolatile memory 123.

The other points in the configuration are similar to those in the endoscopic system 200 according to the second embodiment, so their descriptions are omitted.

In the endoscopic system 300 according to the present embodiment, the following operation is performed at a predetermined timing (such as when a connection has been established between the endoscope 110 and the endoscopic video processor 120), in order to shorten the time needed for a determination of the occurrence of a failure in the endoscope 110 when the occurrence of the failure is suspected.

First, the RFID reader 125 of the endoscopic video processor 120 reads repair information from the RFID tag 113 of the endoscope 110.

Next, the CPU 124 of the endoscopic video processor 120 starts a control of a recording of image information obtained from the endoscope 110 according to a recording condition corresponding to the repair information read by the RFID reader 125, on the basis of the read repair information and a recording condition table read from the nonvolatile memory 123. Specifically, the CPU 124 outputs a recording control command to the moving image encoder 121 such that a compressed file of a moving image having a corresponding moving image density (bit rate) is generated from the image information obtained from the endoscope 110 and the compressed file is recorded in the CF card 122.

The CPU 124 also records, in the CF card 122, the repair information read by the RFID reader 125 at the beginning.

When a predetermined time period has elapsed, the CPU 124 terminates the control described above. Specifically, the CPU 124 outputs a recording control command to the moving image encoder 121 such that the generation and the recording of a compressed file of a moving image are terminated. The predetermined time period can be changed discretionally by the user through the input unit (not illustrated) of the endoscopic video processor 120.

According to the operation described above, repair information on the endoscope 110 and a compressed file of a moving image having a moving image density corresponding to the repair information are recorded in the CF card 122.

According to the endoscopic system 300 of the present embodiment, it is possible to perform a determination of the occurrence of a failure in the endoscope 110 when the occurrence of the failure is suspected, by referring to repair information and a compressed file of a moving image that are recorded in the CF card 122 through the operation described above. Thus, as in the case of the endoscopic system 200 according to the second embodiment, it is possible to shorten the time needed for a determination of the occurrence of a failure in the endoscope 110. As a result, it is also possible to shorten the repair lead time for the endoscope 110.

According to the endoscopic system 300 of the present embodiment, it is also possible to save a recording capacity in the CF card 122 of the endoscopic video processor 120 by including, as information on a recording condition included in a recording condition table, information indicating that a moving image density (bit rate) is to be decreased when image information obtained from the endoscope 110 is recorded, or information indicating that image information is not to be recorded if the number of repairs of the endoscope 110 is within a certain range.

Fourth Embodiment

FIG. 5 illustrates an example of a configuration of the endoscopic system according to a fourth embodiment of the present invention.

For the same components as those in the endoscopic system according to the first embodiment, like reference numbers are used to describe the endoscopic system according to the present embodiment.

As illustrated in FIG. 5, an endoscopic system 400 according to the present embodiment further includes an endoscopic-analysis support system 420 that is connected to the CPU 124 of the endoscopic video processor 120 through a communication network 410.

The communication network 410 is constituted of a wired network or a wireless network or both.

The endoscopic-analysis support system 420 includes a recording unit (not illustrated) in which a serial number (an example of identification information) of an endoscope is recorded, and performs, for example, a management of the endoscope. Further, the endoscopic-analysis support system 420 transmits, to the CPU 124 of the endoscopic video processor 120, a request for a change in a recording condition table.

In the endoscopic system 400 according to the present embodiment, information on a serial number of the endoscope 110 is further recorded in the nonvolatile memory 112 of the endoscope 110.

Further, a table that includes a correspondence relationship between information on a serial number of an endoscope, operation information on the endoscope, and information on a recording condition for image information obtained from the endoscope is recorded in the nonvolatile memory 123 of the endoscopic video processor 120 as a recording condition table. This recording condition table will be described later in detail with reference to FIG. 6.

The CPU 124 performs the following control that is a control based on, for example, the recording condition table recorded in the nonvolatile memory 123. The CPU 124 controls a recording of image information obtained from the endoscope 110 in the CF card 122 according to a recording condition corresponding to a serial number and operation information obtained from the endoscope 110, on the basis of the obtained serial number, the obtained operation information, and the recording condition table recorded in the nonvolatile memory 123.

Further, the CPU 124 changes a portion of or the entirety of the recording condition table recorded in the nonvolatile memory 123 in response to a request for a change in a recording condition table, the request being made by the endoscopic-analysis support system 420.

The other points in the configuration are similar to those in the endoscopic system. 100 according to the first embodiment, so their descriptions are omitted.

FIG. 6 illustrates an example of the recording condition table according to the present embodiment.

As illustrated in FIG. 6, the recording condition table according to the present embodiment is a table that includes a correspondence relationship between a serial number of an endoscope, operation information on the endoscope (information on a total energizing time period), and information on a recording condition for image information obtained from the endoscope.

In the example of FIG. 6, a correspondence relationship between operation information on an endoscope and information on a recording condition for image information obtained from the endoscope is specified for each serial number of an endoscope. For example, when the serial number of an endoscope is "○○○○○", the recording condition is that the image information obtained from the endoscope is recorded as a compressed file of a moving image of 5 Mbps, or the obtained image information is not recorded, or the obtained image information is recorded as a compressed file of a moving image of 10 Mbps, according to the operation information on the endoscope.

In the endoscopic system 400 according to the present embodiment, the CPU 124 of the endoscopic video processor 120 changes a recording condition table recorded in the nonvolatile memory 123 according to a request for a change in a recording condition table, the request being made by the endoscopic-analysis support system 420.

Further, in the endoscopic system 400 according to the present embodiment, the following operation is performed at a predetermined timing (such as when a connection has been established between the endoscope 110 and the endoscopic video processor 120), in order to shorten the time needed for a determination of the occurrence of a failure in the endoscope 110 when the occurrence of the failure is suspected.

First, the CPU 124 of the endoscopic video processor 120 reads a serial number and operation information from the nonvolatile memory 112 of the endoscope 110 and reads a recording condition table from the nonvolatile memory 123.

Next, the CPU 124 determines whether the read recording condition table includes a recording condition for image information that corresponds to the read serial number and the read operation information.

Here, when a result of the determination is "Yes", the CPU 124 performs the following control, and when the result of the determination is "No", it does not perform the control.

In other words, when the result of the determination is "Yes", the CPU 124 starts a control of a recording of image information obtained from the endoscope 110 according to a recording condition corresponding to the read serial number and the read operation information, on the basis of the read serial number, the read operation information, and the read recording condition table. Specifically, the CPU 124 outputs a recording control command to the moving image encoder 121 such that a compressed file of a moving image having a corresponding moving image density (bit rate) is generated from the image information obtained from the endoscope 110 and the compressed file is recorded in the CF card 122.

For example, when the read serial number is "○○○○○", when a read total energizing time period (operation information) is 5000 hours or more, and when the read recording condition table is the recording condition table illustrated in FIG. 6, the CPU 124 outputs a recording control command to the moving image encoder 121 such that a compressed file of a moving image of 10 Mbps is generated and recorded.

The CPU 124 also records, in the CF card 122, the operation information read from the nonvolatile memory 112 of the endoscope 110 at the beginning.

When a predetermined time period has elapsed, the CPU 124 terminates the control described above. Specifically, the CPU 124 outputs a recording control command to the moving image encoder 121 such that the generation and the recording of a compressed file of a moving image are terminated. The predetermined time period can be changed discretionally by a user through the input unit (not illustrated) of the endoscopic video processor 120.

According to the operation described above, only when a recording condition table includes a recording condition for image information that corresponds to a serial number and operation information, operation information on the endoscope 110 and a compressed file of a moving image having a moving image density corresponding to the serial number of the endoscope 110 and the operation information are recorded in the CF card 122.

The endoscopic system 400 of the present embodiment makes it possible to record operation information and a compressed file of a moving image only for a specific endoscope. For example, it is possible to perform the control described above only for an endoscope whose number of repairs is large if a request made by the endoscopic-analysis support system 420 is configured such that a recording condition table only includes information on a serial number of the endoscope whose number of repairs is large (whose number of repairs is not less than a predetermined number of repairs) as information on a serial number of an endoscope that is included in a recording condition table.

Thus, it is possible to perform a determination of the occurrence of a failure in the endoscope 110 when the endoscope 110 is a specific endoscope and when the occurrence of the failure is suspected in the endoscope 110, by referring to operation information and a compressed file of a moving image that are recorded in the CF card 122 through the operation described above. Therefore, there is no need to collect, as is conventionally done, the endoscope 110 and the endoscopic video processor 120 from a place where the endoscopic system 400 is operated, so it is possible to shorten the time needed for a determination of the occurrence of a failure in the endoscope 110. As a result, it is also possible to shorten the repair lead time for the endoscope 110.

According to the endoscopic system 400 of the present embodiment, it is also possible to save a recording capacity in the CF card 122 of the endoscopic video processor 120 by including, as information on a recording condition included in a recording condition table, information indicating that a moving image density (bit rate) is to be decreased when image information obtained from the endoscope 110 is recorded, or information indicating that image information is not to be recorded if a total operation time period of the endoscope 110 is within a certain range.

The endoscopic systems according to the first to fourth embodiments have been described, and the following modification may be made to the endoscopic system according to each of the embodiments.

For example, in the endoscopic system according to each of the first and second embodiments, the log information on the endoscope 110 that is recorded in the CF card 122 of the endoscopic video processor 120 is not limited to information on a current value and a temperature inside an endoscope, but it may be at least one of the information on a current value, the information on a temperature, and the other information with respect to the inside of the endoscope. However, in this case, the recording condition table is configured to include a recording condition for a corresponding piece of log information.

For example, in the endoscopic system according to each of the first and second embodiments, a recording condition for log information may be deleted from the recording condition table so that the CPU 124 of the endoscopic video processor 120 does not obtain and record log information on the endoscope 110.

For example, in the endoscopic system according to each of the third and fourth embodiments, a recording condition for log information may be added to the recording condition table so that the CPU 124 of the endoscopic video processor 120 further obtains and records log information on the endoscope 110.

For example, in the endoscopic system according to each of the second and third embodiments, repair information recorded in the CF card 122 of the endoscopic video processor 120 may further include information on details of repair.

For example, in the endoscopic system according to the third embodiment, a wireless communication method other than a method using a RFID tag or a RFID reader may be used as a method for wirelessly obtaining, from the endoscope 110, repair information recorded in the CF card 122 of the endoscopic video processor 120.

For example, the endoscopic system according to the second embodiment may be configured such that repair information recorded in the CF card 122 of the endoscopic video processor 120 is obtained wirelessly from the endoscope 110, as in the case of the endoscopic system according to the third embodiment.

For example, in the endoscopic system according to the fourth embodiment, the CPU 124 of the endoscopic video processor 120 may change a recording condition table by replacing a recording condition table recorded in the nonvolatile memory 123 with the recording condition table after a change that is transmitted from the endoscopic-analysis support system 420.

For example, in the endoscopic system according to the fourth embodiment, the recording condition table is not limited to the example of FIG. 6, but one correspondence relationship between operation information on an endoscope and information on a recording condition for image information obtained from the endoscope may be specified with respect to one or a plurality of serial numbers of endoscopes.

For example, in the endoscopic system according to each of the first to fourth embodiments, the configuration(s) and the operation(s) of the endoscopic system(s) according to one or more embodiments other than the embodiment may be added.

The embodiments described above are just examples to facilitate understanding of the present invention, and the invention is not limited to these embodiments. Various modifications and alterations may be made hereto without departing from the spirit of the invention specified in the claims.

What is claimed is:

1. An endoscopic system comprising:
an endoscope that obtains image information inside a subject;
a first memory into which the image information obtained from the endoscope is written;
a second memory that has a table in which a predetermined recording condition for writing the image information obtained from the endoscope into the first memory has been recorded prior to receipt of the image information by the first memory from the endoscope, wherein a plurality of different predetermined recording conditions that are each associated with a different one of predetermined operation time periods of the endoscope are recorded in the table; and
a processor configured to obtain, on the basis of an operation time period obtained from the endoscope, the predetermined recording condition associated with the obtained operation time period from among the plurality of predetermined recording conditions recorded in the table of the second memory, and records the image information in the first memory under the predetermined recording condition.

2. The endoscopic system according to claim 1, wherein the first memory is a portable recording medium that is configured to be attachable to and removable from the processor.

3. The endoscopic system according to claim 1, wherein the first memory includes log information on a predetermined parameter that is obtained from the endoscope in addition to the image information obtained from the endoscope.

4. The endoscopic system according to claim 3, wherein the log information on a predetermined parameter includes information on a current value and/or a temperature inside the endoscope that is obtained from the endoscope.

5. The endoscopic system according to claim 1, wherein when the operation time period obtained from the endoscope is less than a first operation time period, the processor records the image information in the first memory with a predetermined compression ratio, and when the operation time period obtained from the endoscope is not less than a second operation time period that is greater than the first operation time period, the processor records the image information in the first memory with a compression ratio higher than the predetermined compression ratio.

6. The endoscopic system according to claim 5, wherein when the operation time period obtained from the endoscope is greater than or equal to the first operation time period and less than the second operation time period, the processor does not record the image information in the first recording medium.

7. The endoscopic system according to claim 1, wherein the processor is further configured to change the table recorded in the second memory.

8. The endoscopic system according to claim 1, wherein the predetermined operation time periods commence from energization of the endoscope.

9. An image processing device that is configured to be connected to an endoscope and obtains image information inside a subject from the endoscope, the image processing device comprising:
a first memory into which the image information obtained from the endoscope is written;
a second memory that has a table in which a predetermined recording condition for writing the image information obtained from the endoscope into the first memory has been recorded prior to receipt of the image information by the first memory from the endoscope, wherein a plurality of different predetermined recording conditions that are each associated with an operation time period of the endoscope are recorded in the table; and
a processor configured to obtain, on the basis of an operation time period obtained from the endoscope, the predetermined recording condition associated with the obtained operation time period from among the plurality of predetermined recording conditions recorded in the table of the second memory, and records the image information in the first memory under the predetermined recording condition.

* * * * *